Figure 1:
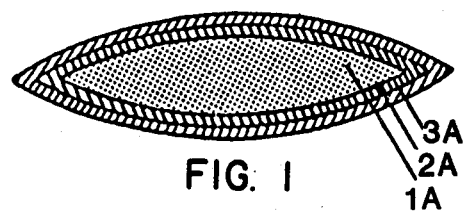

United States Patent [19]

Colombo et al.

[11] Patent Number: 4,681,755
[45] Date of Patent: Jul. 21, 1987

[54] DELIVERY DEVICE FOR ZERO-ORDER RELEASE OF AN ACTIVE PRINCIPLE INTO A DISSOLUTION FLUID AND PROCESS FOR ITS PREPARATION

[75] Inventors: Paolo Colombo, Pavia; Ubaldo Conte, Varese; Alberto Reiner, Como, all of Italy

[73] Assignee: Sigma-Tau Industrie Farmaceutiche Riunite S.p.A., Rome, Italy

[21] Appl. No.: 757,601

[22] Filed: Jul. 22, 1985

[30] Foreign Application Priority Data

Jul. 26, 1984 [IT] Italy .................... 48632 A/84

[51] Int. Cl.⁴ .................... A61K 9/22; A61K 9/32
[52] U.S. Cl. .................... 424/486; 514/965; 424/487
[58] Field of Search .................... 514/965; 424/19, 20, 424/22, 15

[56] References Cited

U.S. PATENT DOCUMENTS

| | | | |
|---|---|---|---|
| 3,275,519 | 9/1966 | Glassman | 424/19 |
| 3,577,512 | 5/1971 | Shepherd et al. | 424/19 |
| 3,832,252 | 8/1974 | Higuchi et al. | 424/19 |
| 4,118,336 | 10/1978 | Morishita et al. | 424/22 |
| 4,173,626 | 11/1979 | Dempski et al. | 424/22 |
| 4,180,560 | 12/1979 | Katz et al. | 424/19 |
| 4,218,433 | 8/1980 | Kooichi et al. | 424/19 |
| 4,309,405 | 1/1982 | Guley et al. | 424/19 |
| 4,539,198 | 9/1985 | Powell et al. | 424/22 |
| 4,557,925 | 12/1985 | Lindahl et al. | 424/19 |

FOREIGN PATENT DOCUMENTS 58-35110  3/1983  Japan .................... 424/19

*Primary Examiner*—Ronald W. Griffin
*Attorney, Agent, or Firm*—Bruce M. Collins

[57] ABSTRACT

A delivery device for zero-order release of an active principle into a dissolution fluid includes a reservoir consisting of a solid matrix of a homogeneous mixture of a polymer material, at least a portion of the active principle and an additive soluble in the dissolution fluid with negative heat of solution, a coating on the solid matrix-type reservoir of a first, release rate-controlling insoluble membrane which modulates the active principle release according to the desired kinetics; and a second, protective membrane on the release rate-controlling membrane of a soluble polymer material.

16 Claims, 2 Drawing Figures

DELIVERY DEVICE FOR ZERO-ORDER RELEASE OF AN ACTIVE PRINCIPLE INTO A DISSOLUTION FLUID AND PROCESS FOR ITS PREPARATION

The present invention relates to a delivery device for zero-order release, i.e. at constant release rate, of an active principle in a fluid phase wherein the active principle is either inherently soluble or can be solubilized.

This constant release rate regimen is described mathematically by the equation $$dQ/dt = \text{constant}$$

where $dQ/dt$ is the release rate, and $Q$ is the amount of substance released at time $t$; or alternatively, in integrated form, as $$Q = \text{constant} \cdot t$$

which shows that the amount of released substance is a linear function of time.

The term "active principle" is used herein and is intended to be construed in its broadest sense as encompassing any chemical substance or composition which will produce a bioactive or pharmacological response either at the site of application or at a site remote therefrom. Insecticides, fertilizers, pharmaceuticals and nutrients are, therefore, included, although not as limiting examples, within the intended meaning of "active principle".

The need of providing means suitable for releasing an active principle according to a programmed release scheme into an environment wherein the substance is intented to be active has long been felt in several technological sectors such as, e.g. the insecticide, fertilizer, pharmaceutical and health food industries.

The purpose of a programmed release is to achieve selectivity and accuracy in delivering the optimum dose of bioactive substance to the desired target, while negligibly affecting non-target sites, at preselected times and for as long as it may be desirable in order to maximize effectiveness.

In the agricultural field, one goal, for instance, is that of providing an intense and prolonged insecticidal activity, while minimizing pollution to soil and water. In the pharmacological field, a goal is to maintain the plasma level of a drug constantly within the therapeutically effective range for a long time, etc.

Among the controlled release systems and devices, those with constant release rate (zero-order release rate) have raised particular interest.

Although the applicability of the device of the present invention is by no means confined to the pharmaceutical field, reference will be hereinbelow made for simplicity sake to the administration of therapeutically effective substances in which the need for providing zero-order release dosage forms is particularly important.

For application in the pharmaceutical field, the device of the present invention may take one of the usual dosage forms of administration, such as tablets, capsules, lozenges, discoids, rectal and vaginal suppositories, globuli and the like. Several so-called "sustained release" or "slow-release" dosage forms are available in the market. However, the pharmacokinetic analysis of blood samples drawn from patients who have been administered such forms shows the presence of a peak of plasma concentration (which frequently causes untoward side-effects) followed by a sudden drop of concentration, well below the threshold of therapeutical effectiveness. At best a certain prolongation of the therapeutical activity may be attained but the drawbacks of conventional immediate release administration forms are not eliminated.

Recently, an orally administrable indomethacin-containing pharmaceutical composition has been marketed, which releases the active principle at constant release rate. This novel administration form (OROS) comprises a core tablet containing drugs and excipients, at least one of them having osmotic activity, which is coated with a semipermeable polymer membrane. The membrane is permeable only to water and is provided with a small orifice. After ingestion, the osmotic agent in the core causes an influx of water which effects dissolution of the drug. The osmotic pressure differential brings about outflow of a saturated drug solution from the orifice. As long as undissolved drug and/or osmotic agent remains, the pressure gradient is constant and the drug delivery rate through the orifice remains zero order.

Because of continued decrease of drug content in the system with time, however, the drug solution becomes less than saturated and the osmotic pressure gradient and the drug delivery rate decline exponentially toward zero. The system ceases to function when iso-osmotic conditions set in.

Although about 70% of the drug content is actually released in zero-order fashion, this system presents the serious drawback to channel the whole drug solution through the orifice in the membrane.

This extremely specific localization of the release of active principle and its high concentration (saturated drug solution outflow taking place only from a practically punctiform area of the OROS tablet) can bring about, particularly when the active principle is as aggressive as indomethacin, damage to the gastric mucosa areas which are exposed to or are located in the close proximity to the release drug.

The main object of the present invention is to provide a delivery device for zero-order release of an active principle which does not present the drawbacks of the known devices and systems.

Figure 2:
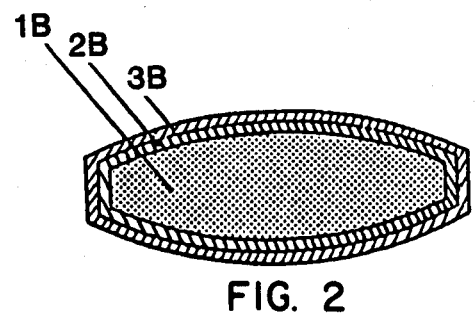

According to the present invention, and with reference to FIGS. 1 and 2 which are longitudinal cross-sectional views of two embodiments, the delivery device for zero-order release of an active principle into a dissolution fluid therefor comprises a solid matrix-type reservoir 1A and 1B formed of a polymer material which is insoluble and unswellable in the dissolution fluid. The reservoir is porous, at least a portion of the active principle being dispersed in the pores of the reservoir. The reservoir comprises a tablet formed of a homogeneous mixture of the polymer material, the active principle, and an additive which is soluble into the dissolution fluid with negative heat of solution.

A coating uniformly surrounds the reservoir. This coating comprises two membranes.

The first, release rate-controlling, membrane 2A and 2B is homogeneous and continuously wraps the reservoir and is formed of a film-forming polymer material insoluble in the dissolution fluid and permeable to the substance. The thickness of the first membrane is determined by the equation thickness = $h = D \cdot S \cdot C_S / R$ wherein:
  D is the constant of diffusion across the membrane;
  S is the surface area through which diffusion occurs;
  $C_S$ is the saturation concentration of the substance in the dissolution fluid; and
  R is the substance release rate.

The second, protective, membrane 3A and 3B is homogeneous and continuously wraps the release rate-controlling membrane, the protective membrane being formed of a film-forming polymer material soluble in the dissolution fluid.

Particularly relevant for the purposes of the present invention is the thickness, h, of the release rate-controlling membrane. Thickness, h, is deduced from Fick's law. Fick's law establishes that once steady-state conditions are attained, the release rate remains constant and independent of time if a solute is confined within a "reservoir" surrounder by a continuous polymer membrane and the thermodynamical activity of the solute is kept constant within the reservoir. When the energy of the system is the solute diffusion energy across the membrane, Fick's law is represented by $$dQ/dt = R = D \cdot S \cdot C_S / h$$

Since D, S, $C_S$ and h are assumed to remain constant, the amount of solute which diffuses across the membrane per time unit is constant, i.e. diffusion occurs according to zero-order kinetics.

The operation of the device of the present invention may be described as follows.

The dissolution fluid, for example body fluids, first dissolves the protective membrane and hydrates the release rate-controlling membrane. The dissolution fluid then penetrates inside the solid reservoir and dissolution of the active principle thus begins, either because it is inherently soluble or because its dissolution is promoted by the "in situ" presence of suitable buffer agents, as it will illustrated in greater detail below. Thereafter, the concentration of the inner solution will reach the saturation value, $C_S$. From this moment on so long as the active principle concentration remains equal to $C_S$, the amount released from the surface of the delivery rate-controlling membrane will be directly proportional to the time; i.e. the release will be according to zero-order release kinetics. In contrast, the solid reservoir if uncoated would release the active principle proportionally to the square root of time (Higuchi's law).

It is apparent that in order to maintain as long as possible the conditions determining the zero-order kinetics, it is essential that the active principle concentration remain substantially equal to $C_S$, and that the pH inside the system, the diffusion coefficient, the surface area and thickness of the delivery rate-controlling membrane remain substantially constant during the device life-span.

These objects are attained by the present invention through both the suitable selection of polymer materials for the solid reservoir and the delivery rate-controlling membrane, and the selection of appropriate additives, particularly the additives which promote the formation of the channel network throughout the solid reservoir, buffer the active principle solution, inhibit the solid reservoir swelling, and plasticize the delivery rate-controlling membrane. Specifically, the qualitative and quantitative composition of the solid reservoir is mainly governed by the active principle solubility, as it will be apparent by the following detailed description of the various embodiments of the invention and the respective roles of their components.

SOLID MATRIX-TYPE RESERVOIR

The solid matrix-type reservoir preferably comprises from 3 to 20% by weight of polymer material; from 30 to 90% by weight of active principle; and from 5 to 50% by weight of an additive soluble into the dissolution fluid with negative solution heat.

The polymer material should be unswellable and insoluble in the active principle's dissolution fluid in order to avoid alterations of the release rate-controlling membrane as by cracking and, for pharmaceutical dosage forms, also biocompatible. Typical materials include cellulose acetate, high viscosity hydroxypropylmethyl cellulose, cellulose acetate propionate, ethyl cellulose and polymethacrylates.

The additive soluble in the dissolution fluid with negative heat of solution generally is a polyol, including sugars, such as mannitol, dextrose, sorbitol, xylitol and the like. Both the role played by this additive and amount thereof are strictly dependent on active principle's solubility. However, also an acid, e.g. citric acid, can be used.

When the active principle is soluble in the dissolution fluid, the additive acts mainly as a plasticizer towards the release rate-controlling membrane.

The negative heat of solution is an essential property of the additive in order that it can act as plasticizer, avoiding a reservoir volume increase and resultant release rate-controlling membrane modification.

When the active principle is sparingly soluble, the additive also plays the role of promoting the formation of a channel network in the solid reservoir, thus gradually increasing its porosity. Consequently, both the dissolution process of the active principle and its ease of reaching the inner surface of the membrane through the channels filled with dissolution fluid are maximized. This contributes to maintaining the active principle concentration in the solution inside the system equal to the saturation value, $C_S$.

When the additive acts solely as plasticizer, it is sufficient that the solid reservoir contains from about 5 to about 15% by weight of additive whereas, when it also acts as channeller, the solid reservoir will contain from about 15 to 50% by weight of additive.

When the active principle is soluble, it itself acts as channeller. When the active principle is sparingly soluble dissolution then is favoured by the presence of the additive additive channeller. In either case, the porosity of the solid reservoir increases as more and more of the active principle dissolves without, however, the outer dimensions of the solid reservoir being thereby affected.

If the active principle's solubility is influenced by the pH of the dissolution liquid, the solid reservoir will conveniently include one or more suitable buffer agents which will be selected, according to criteria well-known in this art, depending on the chemico-physical characteristics of the bioactive substance to be solubilized. The system inner pH consequently will remain substantially constant, again favouring the uniform dissolution of the active principle. In such instances the solid matrix-type reservoir conveniently will contain up to 30% by weight, preferably from 5 to 20% by weight, of the buffering agent.

RELEASE RATE-CONTROLLING MEMBRANE

The polymer material of the first, release rate-controlling, membrane must be a film-forming polymer which is permeable to the active principle but insoluble in the dissolution fluid. These are essential prerequisites so that the membrane features, particularly its thickness and surface area, are not subject to alterations which would in turn affect the release kinetics of the active principle. The polymer also must be biocompatible for pharmaceutical dosage forms.

Suitable polymer material of the release rate-controlling membrane include vinyl polymers and copolymers, celluloses cellulose acetate, hydroxy-propylmethylcellulose, cellulose acetate propionate, ethylcellulose, acrylic polymers and copolymers and the like.

In order that the characterizing features of the release rate-controlling membrane do not vary with time, the plasticizing action exerted on this membrane by the additive with a negative heat of solution contained in the solid reservoir is essential. The release rate-controlling membrane itself may contain a further plasticizer, e.g. dimethylpolysiloxane or castor oil.

The thickness of the release rate-controlling membrane is determined by the previously mentioned equation. Generally, the thickness will be between 0.04 and 0.01 mm. In practice, the thickness conveniently can be expressed as milligrams of coating/cm$^2$ of surface active area of solid reservoir, a suitable coating corresponding to 4–8 mg/cm$^2$.

PROTECTIVE MEMBRANE

The polymer material of the second, protective, membrane must be a film-forming polymer, easily soluble or dispersable in the dissolution liquid. Again for pharmaceutical dosage forms, this polymer should be biocompatible.

Preferably the polymer material of the protective membrane is a soluble cellulose derivative, most preferably low viscosity hydroxypropylmethylcellulose.

A portion of the active principle may be incorporated into the polymer material of the protective member so as to allow the active principle to become immediately available (e.g. in order to rapidly reach the therapeutically effective plasma level), thereby compensating for the time lag in the active principle release. This time lag is obviously related to the time which is necessary for the release rate-controlling membrane to become hydrated and the proper working equilibrium conditions in the device to be attained. For this purpose from 5 to 20% by weight of the active principle can be incorporated into the protective membrane.

As previously stated, biocompatible polymer materials will be used for the manufacture of pharmaceutical dosage forms. The exhausted delivery device will, therefore, be easily removed. It also is possible to utilize biodegradable polymers, provided that during the "life" of the device (e.g. for at least 10 to 12 hours following oral administration) no noteworthy degradation phenomena occur.

According to an embodiment which is particularly preferred in the case of an orally administrable pharmaceutical dosage form, the device of this invention takes on the shape of a biconvex discoid. FIGS. 1 and 2 show the longitudinal cross-sectional views of two such embodiments.

Preferably, the solid matrix-type reservoir of the biconvex discoid has diameter comprised between 6 and 16 mm; the bending radius of the spherical segments of the biconvex discoid is from 10 to 18 and the diameter:-thickness ratio of the biconvex discoid is from 2 to 5.

In the case the amount of active principle contained in the dosage unit is below about 200 mg, the edges of the opposed spherical segments are substantially in mating relationship to each other and the discoid assumes the flat, lenticular shape shown in FIG. 1.

When the amount of active principle exceeds 200 mg/dosage unit, the discoid takes on the customary shape illustrated in FIG. 2, the discoid comprising a cylindrical body with the spherical segments above and below the cylindrical body.

The present invention also comprises a process for manufacturing the previously illustrate device. The process is characterized in that it comprises the following steps:

(1) Mixing the active principle and the additive soluble in the dissolution fluid with negative heat of solution with a solution of the polymer material of the solid matrix-type reservoir in an organic solvent, granulating, drying and adding a lubricant to the dried granulate;

(2) compressing the mixture of step (1) in a tablet press according to known techniques at a pressure of 2500–4000 Kg/cm$^2$, thus obtaining the solid matrix-type reservoir;

(3) Applying the release rate-controlling membrane onto the reservoir by contacting the reservoir of step (2) with a phase containing the first film-forming polymer; and (4) Applyin the protective membrane onto the reservoir coated with the release rate-controlling membrane, by contacting the product of step (3) with a phase containing the second film-forming polymer.

Steps (3) and (4) can be carried out in a pan according to known procedures. In such cases, the first and second film-forming polymer can be applied as solutions in organic solvents. Alternatively, steps (3) and (4) can be carried out according to well-known fluid bed techniques.

The device of the present invention presents several advantages over the prior art devices.

At least 70% by weight of the active principle is released with zero-order kinetics, in most cases in 4–8 hours. This can be demonstrated quantitatively in in vitro models. Moreover, the release of active principle takes place over the whole surface of the device, not from a limited zone thereof. Consequently, the flux of the active principle solution at the outer surface of the device is slower than the flux presented by prior art devices and the danger of an excessive level of active principle being released in a limited environment is thus minimized. Unintentional rupture of the release rate-controlling membrane is extremely unlikely because of the dimensional stability of the solid reservoir and membrane and the plasticized condition of this latter. However, even if the membrane did rupture, this event would not bring about a sudden release ("dose dumping") of active principle whole content into the environment. The solid reservoir merely would release the active principle at a rate proportional to the square root of time, behaving as controlling modulator of the release.

The active principle solubility also is widely independent of the dissolution fluid pH and possible variations thereof, the pH of the saturated solution of active principle within the device remaining practically unchanged.

Finally remarkable stability and strength during handling and storage of the device is achieved, in part because of the protective membrane.

The following non-limiting examples illustrate typical delivery devices according to the invention wherein the active principle is an orally administrable drug. In these specific examples the device takes on the typical shape of a biconvex discoid tablet.

EXAMPLE 1

Preparation of tablets of the lysine salt of indomethacin (a) Preparation of the solid matrix-type reservoirs In order to prepare 1,000 solid matrix-type reservoirs, the following amounts of products were used:
Lysine salt of indomethacin (active principle): 100 g;
Cellulose acetate propionate (average molecular weight ≃75,000) Eastman Kodak, 482-20 type: 10 g;
Disodium phosphate: 80 g;
Mannitol: 70 g;
Talc: 60 g;
Magnesium stearate: 3 g.

The active principle, sodium phosphate, mannitol and talc were fed into a powder mixer and thoroughly mixed therein until a completely homogeneous mixture was obtained.

A solution of the polymer material in 55 ml of 1:1 acetone:isopropanol was prepared. The previously obtained powder mixture then was wetted with this solution. The resulting material was granulated through a 800μ sieve, dried and then granulated again through a 420μ sieve.

The granulate thus obtained was mixed with magnesium stearate and subjected to compression by means of recessed punches having diameter of 12 mm, at the pressure of 3,000 Kg/cm$^2$, thereby producing biconvex, lenticular solid matrix-type reservoirs (see FIG. 1).

The geometrical features of such reservoirs were the following:
diameter: 12 mm;
bending radius of the spherical segments forming the biconvex reservoir: 14 mm;
diameter: thickness ratio: 4;
exposed surface area:
  area of one spherical segment: 1.15 cm$^2$;
  area of the pair of spherical segments: 2.30 cm$^2$;
  area of the lateral surface: 0.30 cm$^2$;
  overall surface area: 2.60 cm$^2$.

(b) Application of the release rate-controlling membrane

In order to apply the drug release rate-controlling membrane, the following products were used:
low permeability acrylic polymer (EUDRAGIT® RS, Röhm Pharma): 4.5 g;
high permeability acrylic polymer (EUDRAGIT® RL, Röhm Pharma): 18.2 g;
castor oil: 0.6 g;
acetone: 110 ml;
isopropanol: 110 ml.

The release rate-controlling membrane was applied in a pan by spraying the polymer solution in short bursts followed by drying intervals with cold air.

The thickness of the release rate-controlling membrane was 0.06 mm, corresponding to 5.4 mg of coating/cm$^2$ of surface area of biconvex solid matrix-type reservoir.

(c) Application of the protective membrane

In order to apply the protective membrane, the following products were used:
hydroxypropyl methyl cellulose (Pharmacoat 606, Shin Etsu Chemical): 3.0 g
titanium dioxide: 1.0 g;
magnesium carbonate: 2.5 g;
indomethacin lysinate: 5.0 g;
solvent mixture (acetone:isopropanol 1:1): 88 ml.

The polymer solution for applying the protective membrane was applied in a pan onto the solid matrix-type reservoirs coated with the release rate-controlling membrane from the previous step.

In the polymer solution for applying the protective membrane, 10% by weight of the total active principle was added. The kinetics features of the indomethacin lysinate release were determined both in "in vitro" models and "in vivo".

"IN VITRO" MODEL

"In vitro" experiments were carried out both on (i) the uncoated solid matrix-type reservoirs, and (ii) the finished devices; i.e., on the reservoirs coated both with the release rate-controlling membrane and with the protective membrane loaded with a portion of the active principle which is desired to be immediately available.

To carry out such experiments, a USP XXI "paddle" apparatus was used with distilled water at 37° C. as the dissolution medium.

The results were as follows:

A—Indomethacin lysinate release from the solid matrix-type reservoir:

| Time (min.) | Total drug released (mg) | Rate (mg/hr) |
| --- | --- | --- |
| 30 | 20 | 40 |
| 60 | 54 | 54 |
| 90 | 65 | 43 |
| 120 | 75 | 37.5 |

B—Indomethacin lysinate release from the solid matrix-type reservoir coated with both the release rate-controlling membrane and protective membrane loaded with a portion of the drug:

| Time (hours) | Total drug released (mg) | Rate (mg/hr) |
| --- | --- | --- |
| 1 | .14 | 14 |
| 2 | 25 | 12.5 |
| 3 | 40 | 13.3 |
| 4 | 57 | 14.25 |
| 5 | 77 | 15.4 |
| 6 | 93 | 15.5 |

The foregoing results demonstrate that the drug is wholly released from the solid matrix-type reservoir in about 5 hours. After the release rate-controlling membrane is applied, the release rate "in vitro" remains substantially constant through the sixth hour.

"IN VIVO" EXPERIMENTS

A healthy volunteer was administered the same device. The following plasma levels of active principle were detected.

| Time (hours) | mcg/ml |
| --- | --- |
| 1 | 1.6 |
| 2 | 2.5 |

-continued

| Time (hours) | mcg/ml |
| --- | --- |
| 5 | 3.2 |
| 8 | 1.5 |
| 12 | 1.1 |
| 24 | 0.8 |

EXAMPLE 2

Preparation of tablets of methisoprinol (a) Preparation of the solid matrix-type reservoirs In order to prepare 1,000 solid matrix-type reservoirs, the following amounts of products were used:
methisoprinol (active principle): 500 g;
cellulose acetate propionate (as in Example 1): 25.0 g;
mannitol: 10 g;
magnesium stearate: 8.0 g.

Compounding, granulation and compression procedures as in Example 1.

The geometrical features of the solid matrix-type reservoirs thus obtained (see FIG. 2) were identical to those of the embodiment in Example 1, except that the area of the side wall was 1.32 cm$^2$, total area was 3.62 cm$^2$ and the diameter: thickness ratio was 2.

(b) Application of the release rate-controlling membrane

Solution of polymer material and application procedures as in Example 1. The membrane thickness was 0.07 mm, corresponding to 6 mg of coating/cm$^2$ surface area of solid reservoir.

(c) Application of the protective membrane

The same procedures as those of Example 1 were followed, except that no active principle was loaded in the protective membrane.

"IN VITRO" MODEL

Procedures and apparatus as in Example 1.

A—Methisoprinol release from the solid matrix-type reservoir:

| Time (min.) | Total drug released (mg) |
| --- | --- |
| 30 | 225 |
| 60 | 312 |
| 90 | 365 |
| 120 | 405 |

B—Methisoprinol release from the solid matrix-type reservoir coated with both the release rate-controlling membrane and the protective membrane:

| Time (hours) | Total drug released (mg) |
| --- | --- |
| 1 | 53 |
| 2 | 115 |
| 3 | 173 |
| 4 | 223 |
| 5 | 273 |
| 6 | 315 |
| 7 | 357 |

EXAMPLE 3

Preparation of tablets of acetyl L-carnitine chloride (a) Preparation of the solid matrix-type reservoirs In order to prepare 1,000 solid matrix-type reservoirs, the following amounts of products were used:
acetyl L-carnitine (active principle): 500 g;
cellulose acetate propionate (as in Example 1): 40 g;
mannitol: 50 g;
talc: 15 g;
magnesium stearate: 10 g.

Compounding, granulation and compression procedures as in Example 1, except that a pressure of 4000 kg/cm$^2$ was used.

Geometrical features of solid reservoirs (see FIG. 2) as in Example 2.

(b) Application of the release rate-controlling membrane

Solution of polymer material and application procedures as in Example 1. The membrane thickness was 0.08 mm, corresponding to 6.5 mg of coating/cm$^2$ surface area of solid reservoir.

(c) Application of the protective membrane

The same procedures as those of Example 1 were followed, except that no active principle was loaded in the protective membrane.

"IN VITRO" MODEL

Procedures and apparatus as in Example 1.

A—Acetyl L-carnitine release from the solid matrix-type reservoir:

| Time (min.) | Total drug released (mg) |
| --- | --- |
| 30 | 158 |
| 60 | 242 |
| 90 | 335 |
| 120 | 395 |

B—Acetyl L-carnitine release from the solid matrix-type reservoir coated with both the release rate-controlling membrane and the protective membrane.

| Time (hours) | Total drug released (mg) |
| --- | --- |
| 1 | 60 |
| 2 | 135 |
| 3 | 210 |
| 4 | 280 |
| 5 | 348 |
| 6 | 411 |

EXAMPLE 4

Preparation of tablets of clometacin lysinate (a) Preparation of the solid matrix-type reservoirs In order to prepare 1,000 solid matrix-type reservoirs, the following amounts of products were used:
clometacin lysinate, corresponding to clometacin (active principle): 150 g;
disodium phosphate: 40 g;
cellulose acetate propionate (as in Example 1): 10 g;
mannitol: 20 g;
talc: 40 g;
magnesium stearate: 5 g.

Compounding, granulation and compression procedures as in Example 1.

Geometrical features of solid reservoirs (see FIG. 1) as in Example 1.

(b) and (c) As in Example 1.

"IN VITRO" MODEL

Procedures and apparatus as in Example 1.

A—Clometacin lysinate release from the solid matrix-type reservoir:

| Time (min.) | Total drug released (mg) |
| --- | --- |
| 30 | 63 |
| 60 | 91 |
| 90 | 105 |
| 120 | 124 |

B—Clometacin lysinate from the solid matrix-type reservoir coated with both the release rate-controlling membrane and protective membrane loaded with a portion of the drug:

| Time (hours) | Total drug released (mg) |
| --- | --- |
| 1 | 15 |
| 2 | 40 |
| 3 | 61 |
| 4 | 78 |
| 5 | 95 |
| 6 | 116 |

EXAMPLE 5

Preparation of tablets of trimebutine (a) Preparation of the solid matrix-type reservoirs In order to prepare 1,000 solid matrix-type reservoirs, the following amounts of products were used:
trimebutine, base (active principle): 140 g;
cellulose acetate propionate (as in Example 1): 10 g;
anhydrous citric acid: 100 g;
mannitol: 45 g;
talc: 35 g;
magnesium stearate: 3 g.

Compounding, granulation and compression procedures as in Example 1.

Geometrical features of solid reservoirs (see FIG. 1) as in example 1.

(b) Application of the release rate-controlling membrane

Solution of polymer material and application procedures as in Example 1. The membrane thickness was 0.05 mm, corresponding to 5 mg of coating/cm² surface area of solid reservoir.

(c) Application of the protective membrane

The same procedures as those of Example 1 were followed.

"IN VITRO" MODEL

Procedures and apparatus as in Example 1.

A—Trimebutine release from the solid matrix-type reservoir:

| Time (min.) | Total drug released (mg) |
| --- | --- |
| 30 | 20 |
| 60 | 64 |
| 90 | 80 |
| 120 | 105 |

B—Trimebutine release from the solid matrix-type reservoir coated with both the release rate-controlling membrane and protective membrane loaded with a portion of the drug:

| Time (hours) | Total drug released (mg) |
| --- | --- |
| 1 | 18 |
| 2 | 30 |
| 3 | 50 |
| 4 | 67 |
| 5 | 90 |
| 6 | 103 |

EXAMPLE 6

Preparation of tablets of trimebutine

Trimebutine tablets according to this invention were also prepared as follows:

(a) Preparation of the solid matrix-type reservoirs

In order to prepare 1,000 solid matrix-type reservoirs, the following amounts of products were used:
trimebutine, base: 135 g;
ethylcellulose: 25 g;
anhydrous citric acid: 100 g;
talc: 44 g;
magnesium stearate: 1 g.

Trimebutine, citric acid, talc and 18.0 g of ethylcellulose were thoroughly mixed for 20 minutes.

The mixture was kneaded with 70 ml of a 10% ethylcellulose solution in ethylacetate. The resulting mixture was granulated through a 800$\mu$ sieve. The granules were dried, mixed with magnesium stearate and pressed by means of recessed 12 mm punches at 3,000 kg/cm². Geometrical features of the solid reservoirs (see FIG. 1) as in Example 1.

(b) Application of the release rate-controlling membrane

This membrane was applied in a pan by spraying a 6-8% solution of 4:1 Eudragit RL/Eudragit RS in 1:1 isopropanol-acetone, containing 1% by weight of castor oil (22 mg of polymer per reservoir were applied).

(c) Application of the protective membrane

A 6% hydroxypropylmethylcellulose solution in isopropanol-CH$_2$Cl$_2$ (corresponding to 60-70 mg of polymer per reservoir) was used. The solution also contained 15 mg of trimebutine per reservoir.

"IN VITRO" MODEL

The procedures and the apparatus were the same as those of Example 1.

A—Trimebutine release from the solid matrix-type reservoir:

| Time (min.) | Total drug released (mg) |
| --- | --- |
| 20 | 47 |
| 40 | 64.8 |
| 60 | 77.0 |
| 80 | 87.8 |
| 100 | 94.5 |
| 180 | 115 |

B—Trimebutine release from the solid matrix-type reservoir coated with both the release rate-controlling membrane and protective membrane loaded with a portion of the drug:

| Time (hours) | Total drug released (mg) |
| --- | --- |
| 0.5 | 22.5 |
| 1 | 45.0 |
| 2 | 82.5 |
| 3 | 105.0 |
| 4 | 120.0 |

-continued

| Time (hours) | Total drug released (mg) |
|---|---|
| 5 | 127.5 |

EXAMPLE 7

Preparation of diltiazem tablets (a) Preparation of the solid matrix-type reservoirs In order to prepare 1,000 solid matrix-type reservoirs, the following amounts of products were used:
diltiazem HCl (active principle): 120 g;
cellulose acetate propionate (see Ex. 1): 14 g;
mannitol: 20 g;
talc: 183 g;
magnesium stearate: 3 g.

Compounding, granulation and compression procedures as in Example 1: solid reservoirs weighting 340 mg each were obtained; thickness 3.2–3.3 mm.

(b) and (c) Application of release rate-controlling membrane (25 mg of polymer per reservoir) and protective membrane (no active principle loaded therein) as in Example 6.

"IN VITRO" MODEL

A—Diltiazem release from the solid matrix-type reservoir:

| Time (min) | Total drug released (mg) |
|---|---|
| 15 | 40.0 |
| 30 | 57.6 |
| 45 | 69.6 |
| 60 | 80.4 |
| 75 | 85.2 |

B—Diltiazem release from the solid matrix-type reservoir coated with both the release rate-controlling membrane and protective membrane:

| Time (hours) | Total drug released (mg) |
|---|---|
| 0.5 | 14.4 |
| 1 | 29.5 |
| 2 | 67.6 |
| 3 | 89.9 |
| 4 | 102.3 |

What is claimed is:

1. A delivery device which in the presence of a dissolution fluid releases a biologically active principle at a substantially constant rate for an extended period of time, the device comprising
   (a) a reservoir comprising
      (i) a solid porous matrix of homogenous polymeric material which material is insoluble and unswellable in the dissolution fluid, the geometric dimensions of which remain substantially unchanged over said period of time;
      (ii) an additive which is soluble in the dissolution fluid and which has a negative heat of dissolution with respect to said fluid; and
      (iii) the biologically active ingredient, said additive and biologically active ingredient being disposed in the pores of said matrix;
   (b) a first homogenous and continuous coating of a film-forming polymer on said reservoir, said coating maintaining a substantially constant surface area and thickness over said period of time, said polymer being insoluble in said dissolution fluid with said coating being permeable to both said fluid and to a solution of said active ingredient in said fluid, the thickness of said first coating being such as to comply substantially with the relationship:

$$\text{thickness} = D \times S \times C_s / R$$

in which
   D is the diffusion constant of said first coating;
   S is the surface area of said first coating;
   $C_s$ is the saturation constant of the active principle in the dissolution fluid; and
   R is the release rate; and
   (c) a second homogenous and continuous coating of a a film-forming polymer material which is soluble in the dissolution fluid disposed over said first coating.

2. A device according to claim 1 wherein said reservoir includes a buffer.

3. A device according to claim 2 wherein said buffer constitutes up to about 30% by weight of said matrix.

4. A device according to claim 1 wherein said biologically active principle is present in an amount from about 30 to about 90% of the weight of said reservoir.

5. A device according to claim 1 wherein said additive which is soluble in the dissolution fluid with a negative heat of solution is present in an amount of from about 5 to about 50% of the weight of said reservoir.

6. A device according to claim 5 wherein said additive is a polyol or an acid.

7. A device according to claim 6 wherein said additive in mannitol, dextrose, sorbitol, or xylitol.

8. A device according to claim 1 wherein said matrix constitutes from about 3 to about 20% of said reservoir.

9. A device according to claim 8 wherein the polymeric material of said matrix is cellulose acetate, high viscosity hydroxypropylmethyl cellulose, cellulose acetate propionate, ethyl cellulose, or polymethacrylate.

10. A device according to claim 1 wherein said first homogenous and continuous coating is a vinyl polymer or co-polymer, cellulose, cellulose acetate, hydroxypropylmethyl cellulose, cellulose acetate propionate, ethyl cellulose, an acrylic polymer, or an acrylic co-polymer.

11. A device according to claim 1 wherein said second coating is low viscosity hydroxypropylmethyl cellulose.

12. A device according to claim 1 wherein additional active principle is present in said second polymeric coating.

13. A device according to claim 1 wherein a plasticizer is present in said first coating.

14. A device according to claim 1 wherein said biologically active principle is an orally administerable drug.

15. A device according to claim 14 wherein the outer surface of said reservoir is a biconvex discoid defined by the circular intersection of two opposed spherical segments, the discoid having diameter from 6 to 16 mm, the bending radius of the spherical segments of the biconvex discoid being comprised between 10 and 18 mm, the diameter:thickness ratio of the biconvex discoid being comprised between 2 and 5.

16. A device according to claim 14 wherein said reservoir defines an intermediate cylindrical wall segment and two opposed spherical end segments intersecting said cylindrical wall segment.

* * * * *